US007935723B2

(12) United States Patent
Hughes

(10) Patent No.: US 7,935,723 B2
(45) Date of Patent: May 3, 2011

(54) USE OF ORGANIC COMPOUNDS

(75) Inventor: Thomas Edward Hughes, Concord, MA (US)

(73) Assignee: Novartis Pharma AG, Basel (CH)

( * ) Notice: Subject to any disclaimer, the term of this patent is extended or adjusted under 35 U.S.C. 154(b) by 284 days.

(21) Appl. No.: 11/628,546

(22) PCT Filed: Jun. 3, 2005

(86) PCT No.: PCT/EP2005/006003
§ 371 (c)(1),
(2), (4) Date: Dec. 4, 2006

(87) PCT Pub. No.: WO2005/117861
PCT Pub. Date: Dec. 15, 2005

(65) Prior Publication Data
US 2007/0254944 A1 Nov. 1, 2007

Related U.S. Application Data

(60) Provisional application No. 60/577,010, filed on Jun. 4, 2004, provisional application No. 60/604,273, filed on Aug. 25, 2004.

(51) Int. Cl.
*A61K 31/40* (2006.01)
*A61K 31/155* (2006.01)
(52) U.S. Cl. ......... 514/423; 514/428; 514/635; 514/866
(58) Field of Classification Search .................. 514/423, 514/428, 635, 866
See application file for complete search history.

(56) References Cited

U.S. PATENT DOCUMENTS 3,174,901 A * 3/1965 Sterne ........................... 514/635
6,166,063 A * 12/2000 Villhauer ...................... 514/423

FOREIGN PATENT DOCUMENTS
WO WO01/52825 A 7/2001

OTHER PUBLICATIONS

Ahren, Bo et al., "The DDP-4 inhibitor, LAF237, improves glycemic control in patients with type 2 diabetes (T2DM) inadequately treated with metmorfin" Jun. 2004, XP002344251, ADA 64th Scientific sessions Orlando, FL.
Thomson Scientific Meeting Previews, 2004 XP002344252.
Yasuda N et al.: "Enhanced secretion of glucagon-like peptide 1 by biguanide compounds" Biochemical and Biophusical Research Communications, Academic PRES, San Diego, CA, US ISSN: 0006-291X p. 781, p. 783, right-hand column.
Yasuda N et al.: "Synergistic effects of combination of DPPIV inhibitor with metformin on glycemic control, food intake and weight gain in Zucker fa/fa rats." Diabetologia, vol. 46, No. Supplement 2, Aug. 2003, p. A 28f4, XP009053536 & 18th Congress of TE International Diabetes Feeration; Paris, France; Aug. 24-29, 2003 ISSN: 012-186X abstract.

* cited by examiner

*Primary Examiner* — Kevin Weddington
(74) *Attorney, Agent, or Firm* — Ann R. Pokalsky, Esq.; Dilworth & Barrese, LLP

(57) ABSTRACT

A method for improving glucose control by administering metformin in combination with a DPP-IV inhibitor to a patient in need thereof, in an amount sufficient to control the glucose level over an extended period of time.

3 Claims, No Drawings

USE OF ORGANIC COMPOUNDS

This application is the National Stage of Application No. PCT/EP2005/006003, filed on Jun. 3, 2005, which claims benefit under 35 U.S.C. §119(e) of U.S. Provisional Application No. 60/577,010, filed Jun. 4, 2004, and U.S. Provisional Application No. 60/604,273, filed Aug. 25, 2004. The contents of both are incorporated herein by reference in their entirety.

The invention relates to a method of treatment and a diagnostic method, wherein the patient is treated with a Dipeptidyl peptidase IV inhibitor (DPP-IV inhibitor) or a pharmaceutically acceptable salt thereof and metformin over an extended period of time preferably one year or more.

The treated patients are preferably suffering from hyperglycemia such as diabetes mellitus preferably non-insulin-dependent diabetes mellitus or Impaired Glucose Metabolism (IGM) preferably Impaired Glucose Tolerance (IGT).

Diabetes mellitus is a relatively common disorder (estimated at about 1% prevalence in the general population) which is characterized by hyperglycemia. There are three basic types of diabetes mellitus, type I or insulin-dependent diabetes mellitus (IDDM), type II or non-insulin-dependent diabetes mellitus (NIDDM), and type A insulin resistance. Patients with either type I or type II diabetes can become insensitive to the effects of exogenous insulin ("insulin resistant") through a variety of mechanisms. Type A insulin resistance results from either mutations in the insulin receptor gene or defects in post-receptor sites of action critical for glucose metabolism. Diabetes is generally controlled through administration of exogenous insulin (especially in type I diabetics), dietary control and exercise (especially in type II diabetics) or both.

Impaired Glucose Metabolism (IGM) is defined by blood glucose levels that are above the normal range but are not high enough to meet the diagnostic criteria for type 2 diabetes mellitus. The incidence of IGM varies from country to country, but usually occurs 2-3 times more frequently than overt diabetes. Until recently, individuals with IGM were felt to be pre-diabetics, but data from several epidemiologic studies argue that subjects with IGM are heterogeneous with respect to their risk of diabetes and their risk of cardiovascular morbidity and mortality. The data suggest that subjects with IGM, in particular IGT, do not always develop diabetes, but whether they are diabetic or not, they are, nonetheless, at high risk for cardiovascular morbidity and mortality. Among subjects with IGM, about 58% have Impaired Glucose Tolerance (IGT), another 29% have Impaired Fasting Glucose (IFG), and 13% have both abnormalities (IFG/IGT). IGT is characterized by elevated postprandial (post-meal) hyperglycemia while IFG has been defined by the ADA (see Table below) on the basis of fasting glycemic values.

The categories of Normal Glucose Tolerance (NGT), IGM and type 2 diabetes mellitus were defined by the ADA (American Diabetes Association) in 1997.

The fact that IGT is an independent risk factor in non-diabetics as well as diabetics justifies it as a new indication, separate from diabetes, for prevention and treatment of cardiovascular morbidity and mortality as well as cancer. Furthermore the stage between normoglycemia and type 2 diabetes mellitus, especially the glycemic stage, is becoming of major interest and there is a strong need for a method to inhibit or delay the progression to type 2 diabetes mellitus, and also the variety of cardiovascular and microvascular conditions and diseases as well as cancer that have been associated with IGM and especially IFG and/or IGT.

Type 2 diabetes is a progressive disease, and although monotherapy may initially control blood glucose in some patients, it is associated with a high secondary failure rate. This high incidence of therapeutic failure is a major contributor to the high rate of long-term hyperglycemia-associated complications in patients with type 2 diabetes. The limitations of single-agent therapy for maintaining glycemic control may be overcome, at least in some patients, and for a limited period of time by combining multiple oral drugs to achieve reductions in blood glucose that cannot be sustained during long-term therapy with single agents. Available data support the conclusion that in most patients with type 2 diabetes, oral monotherapy will fail and treatment with multiple drugs will be required.

But, because Type 2 diabetes is a progressive disease, even patients with good initial responses to combination therapy will eventually require an increase of the dosage or further treatment with insulin because the blood glucose level is very difficult to maintain stable for a long period of time.

Although combination therapy has the potential to enhance glycemic control, it is not without limitations. Many results indicate that the risk for hypoglycemia may increase with combination therapy, and the requirement for multiple medications may also reduce patient compliance. In addition, taking multiple antihyperglycemic drugs increases the potential for pharmacokinetic interactions with other medications that the patient may be taking.

The rational use of oral combination therapy can temporarily delay the need for multiple insulin injections, facilitate temporarily the maintenance of low glucose level or low glycosylated hemoglobin (HbA1c) level and help temporarily to prevent vascular complications.

The applicant has surprisingly discovered that DPP-IV inhibitors especially LAF237 can be used in combination with Metformin to maintain low glucose level or low glycosylated hemoglobin (HbA1c) level over an extended period of time. Furthermore the long term treatment with such a combination has significantly less inconvenient than other combinations.

Metformin, i.e. N,N-dimethylimidocarbonimide diamide, is a known compound approved by the U.S. Food & Drug Administration for the therapeutic treatment of diabetes. The compound and its preparation are disclosed, for example, in U.S. Pat. No. 3,174,901, issued May 23, 1965. It is known that metformin is effective in the treatment of type 2 diabetes, otherwise known as non-insulin-dependent diabetes mellitus (NIDDM).

In the present context the term "metformin" is also intended to comprise any salt or crystal form, especially the metformin hydrochloride salt.

The term "DPP-IV inhibitor" is intended to indicate a molecule that exhibits inhibition of the enzymatic activity of DPP-IV and functionally related enzymes, such as from 1-100% inhibition, and specially preserves the action of substrate molecules, including but not limited to glucagon-like peptide-1, gastric inhibitory polypeptide, peptide histidine methionine, substance P, neuropeptide Y, and other molecules typically containing alanine or proline residues in the second aminoterminal position. Treatment with DPP-IV inhibitors prolongs the duration of action of peptide substrates and increases levels of their intact, undegraded forms leading to a spectrum of biological activities relevant to the disclosed inventions.

DPP-IV can be used in the control of glucose metabolism because its substrates include the insulinotropic hormones Glucagon like peptide-1 (GLP-1) and Gastric inhibitory peptide (GIP). GLP-1 and GIP are active only in their intact forms; removal of their two N-terminal amino acids inactivates them. In vivo administration of synthetic inhibitors of DPP-IV prevents N-terminal degradation of GLP-1 and GIP, resulting in higher plasma concentrations of these hormones, increased insulin secretion and, therefore, improved glucose tolerance. For that purpose, chemical compounds are tested for their ability to inhibit the enzyme activity of purified CD26/DPP-IV. Briefly, the activity of CD26/DPP-IV is measured in vitro by its ability to cleave the synthetic substrate Gly-Pro-p-nitroanilide (Gly-Pro-pNA). Cleavage of Gly-Pro-pNA by DPP-IV liberates the product p-nitroanilide (pNA), whose rate of appearance is directly proportional to the enzyme activity. Inhibition of the enzyme activity by specific enzyme inhibitors slows down the generation of pNA. Stronger interaction between an inhibitor and the enzyme results in a slower rate of generation of pNA. Thus, the degree of inhibition of the rate of accumulation of pNA is a direct measure of the strength of enzyme inhibition. The accumulation of pNA is measured with a spectrophotometer. The inhibition constant, Ki, for each compound is determined by incubating fixed amounts of enzyme with several different concentrations of inhibitor and substrate.

In the present context "a DPP-IV inhibitor" is also intended to comprise active metabolites and prodrugs thereof, such as active metabolites and prodrugs of DPP-IV inhibitors. A "metabolite" is an active derivative of a DPP-IV inhibitor produced when the DPP-IV inhibitor is metabolised. A "prodrug" is a compound that is either metabolised to a DPP-IV inhibitor or is metabolised to the same metabolite(s) as a DPP-IV inhibitor. In the present context the term "a DPP-IV inhibitor" is also intended to comprise pharmaceutical salts thereof.

DPP-IV inhibitors are known in the art. In the following reference is made to representatives of DPP-IV inhibitors:
DPP-IV inhibitors are in each case generically and specifically disclosed e.g. in WO 98/19998, DE19616 486 A1, WO 00/34241, WO 95/15309, WO 01/72290, WO01/52825, WO03/002553, WO 9310127, WO 99/61431, WO 9925719, WO 9938501, WO 9946272, WO 9967278 and WO 9967279.

Preferred DPP-IV inhibitors are described in the following patent applications; WO 02053548 especially compounds 1001 to 1293 and examples 1 to 124, WO 02067918 especially compounds 1000 to 1278 and 2001 to 2159, WO 02066627 especially the described examples, WO 02/068420 especially all the compounds specifically listed in the examples I to LXIII and the described corresponding analogues, even preferred compounds are 2(28), 2(88), 2(119), 2(136) described in the table reporting IC50, WO 02083128 such as in the claims 1 to 5 especially compounds described in examples 1 to 13 and the claims 6 to 10, US 2003096846 especially the specifically described compounds, WO 2004/037181 especially examples 1 to 33, WO 0168603 especially compounds of examples 1 to 109, EP1258480 especially compounds of examples 1 to 60, WO 0181337 especially examples 1 to 118, WO 02083109 especially examples 1A to 1D, WO 030003250 especially compounds of examples 1 to 166, most preferably 1 to 8, WO 03035067 especially the compounds described in the examples, WO 03/035057 especially the compounds described in the examples, US2003216450 especially examples 1 to 450, WO 99/46272 especially compounds of claims 12, 14, 15 and 17, WO 0197808 especially compounds of claim 2, WO 03002553 especially compounds of examples 1 to 33, WO 01/34594 especially the compounds described in the examples 1 to 4, WO 02051836 especially examples 1 to 712, EP1245568 especially examples 1 to 7, EP1258476 especially examples 1 to 32, US 2003087950 especially the described examples, WO 02/076450 especially examples 1 to 128, WO 03000180 especially examples 1 to 162, WO 03000181 especially examples 1 to 66, WO 03004498 especially examples 1 to 33, WO 0302942 especially examples 1 to 68, U.S. Pat. No. 6,482,844 especially the described examples, WO 0155105 especially the compounds listed in the examples 1 and 2, WO 0202560 especially examples 1 to 166, WO 03004496 especially examples 1 to 103, WO 03/024965 especially examples 1 to 54, WO 0303727 especially examples 1 to 209, WO 0368757 especially examples 1 to 88, WO 03074500 especially examples 1 to 72, examples 4.1 to 4.23, examples 5.1 to 5.10, examples 6.1 to 6.30, examples 7.1 to 7.23, examples 8.1 to 8.10, examples 9.1 to 9.30, WO 02038541 especially examples 1 to 53, WO 02062764 especially examples 1 to 293, preferably the compound of example 95 (2-{{3-(Aminomethyl)-4-butoxy-2-neopentyl-1-oxo-1,2 dihydro-6-isoquinolinyl}oxy}acetamide hydrochloride), WO 02308090 especially examples 1-1 to 1-109, examples 2-1 to 2-9, example 3, examples 4-1 to 4-19, examples 5-1 to 5-39, examples 6-1 to 6-4, examples 7-1 to 7-10, examples 8-1 to 8-8, examples 7-1 to 7-7 of page 90, examples 8-1 to 8-59 of pages 91 to 95, examples 9-1 to 9-33, examples 10-1 to 10-20, US 2003225102 especially compounds 1 to 115, compounds of examples 1 to 121, preferably compounds a) to z), aa) to az), ba) to bz), ca) to cz) and da) to dk) WO 0214271 especially examples 1 to 320, US 2003096857, U.S. application Ser. No. 09/788,173 filed Feb. 16, 2001 (attorney file LA50) especially, the described examples, WO99/38501 especially the described examples, WO99/46272 especially the described examples and DE19616 486 A1 especially val-pyr, val-thiazolidide, isoleucyl-thiazolidide, isoleucyl-pyrrolidide, and fumar salts of isoleucyl-thiazolidide and isoleucyl-pyrrolidide.

Further preferred DPP-IV inhibitors include the specific examples disclosed in U.S. Pat. Nos. 6,124,305 and 6,107, 317, International Patent Applications, Publication Numbers WO 9819998, WO 95153 09 and WO 9818763; such as 1[2-[(5 eyanopyridin-2-yl)aminoethylamino]acetyl-2-cyano-(S)-pyrrolidine and (2S)-I-[(2S)-2 amino-3,3-dimethylbutanoyl]-2-pyrrolidinecarbonitrile.

In a further preferred embodiment, the DPP-IV inhibitor is a N-peptidyl-O-aroyl hydroxylamine or a pharmaceutically acceptable salt thereof. Aroyl is, for example, naphthylcarbonyl; or benzoyl which is unsubstituted or mono- or disubstituted, for example, by lower alkoxy, lower alkyl, halogen or, preferably, nitro. The peptidyl moiety comprises preferably two α-amino acids, e.g. glycine, alanine, leucine, phenylalanine, lysine or proline, of which the one attached directly to the hydroxylamine nitrogen atom is preferably proline.

In each case in particular in the compound claims and the final products of the working examples, the subject matter of the final products, the pharmaceutical preparations and the claims are hereby incorporated into the present application by reference to these publications.

WO 9819998 discloses N-(N'-substituted glycyl)-2-cyano pyrrolidines, in particular 1-[2-[5-Cyanopyridin-2-yl] amino]-ethylamino]acetyl-2-cyano-(S)-pyrrolidine.

Preferred compounds described in WO03/002553 are listed on pages 9 to 11 and are incorporated into the present application by reference.

DE19616 486 A1 discloses val-pyr, val-thiazolidide, isoleucyl-thiazolidide, isoleucyl-pyrrolidide, and fumar salts of isoleucyl-thiazolidide and isoleucyl-pyrrolidide.

WO 0034241 and U.S. Pat. No. 6,110,949 disclose N-substituted adamantyl-amino-acetyl-2-cyano pyrrolidines and W (substituted glycyl)-4-cyano pyrrolidines respectively. DPP-IV inhibitors of interest are specially those cited in claims 1 to 4.

WO 9515309 discloses amino acid 2-cyanopyrrolidine amides as inhibitors of DPP-IV and WO 9529691 discloses peptidyl derivates of diesters of alpha-aminoalkylphosphonic acids, particularly those with proline or related structures. DPP-IV inhibitors of interest are specially those cited in Table 1 to 8.

In WO 01/72290 DPP-IV inhibitors of interest are specially those cited in example 1 and claims 1, 4, and 6.

WO01/52825 specially discloses (S)-1-{2-[5-cyanopyridin-2-yl)amino]ethyl-aminoacetyl)-2-cyano-pyrrolidine or (S)-1-[(3-hydroxy-1-adamantyl)amino]acetyl-2-cyano-pyrrolidine (LAF237).

WO 9310127 discloses proline boronic esters useful as DPP-IV inhibitors. DPP-IV inhibitors of interest are specially those cited in examples 1 to 19.

Published patent application WO 9925719 discloses sulphostin, a DPP-IV inhibitor prepared by culturing a *Streptomyces* microorganism.

WO 9938501 discloses N-substituted 4- to 8-membered heterocyclic rings. DPP-IV inhibitors of interest are specially those cited in claims 15 to 20.

WO 9946272 discloses phosphoric compounds as inhibitors of DPP-IV. DPP-IV inhibitors of interest are specially those cited in claims 1 to 23.

Other preferred DPP-IV inhibitors are the compounds of formula I, II or III disclosed in the patent application WO 03/057200 on page 14 to 27. Most preferred DPP-IV inhibitors are the compounds specifically described on pages 28 and 29.

Published patent applications WO 9967278 and WO 9967279 disclose DPP-IV prodrugs and inhibitors of the form A-B-C where C is either a stable or unstable inhibitor of DPP-IV.

Preferably, the N-peptidyl-O-aroyl hydroxylamine is a compound of formula VII

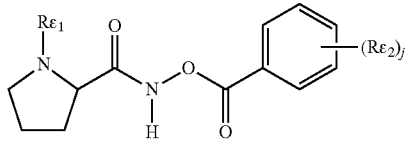

(VII)

wherein
j is 0, 1 or 2;
R$\epsilon_1$ represents the side chain of a natural amino acid; and
R$\epsilon_2$ represents lower alkoxy, lower alkyl, halogen or nitro;
or a pharmaceutically acceptable salt thereof.

In a very preferred embodiment of the invention, the N-peptidyl-O-aroyl hydroxylamine is a compound of formula VIIa

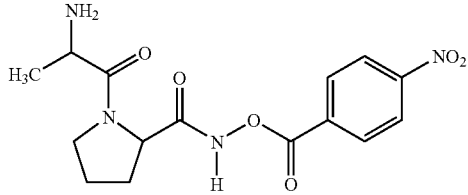

(VIIa)

or a pharmaceutically acceptable salt thereof.

N-Peptidyl-O-aroyl hydroxylamines, e.g. of formula VII or VIIa, and their preparation are described by H. U. Demuth et al. in J. Enzyme Inhibition 1988, Vol. 2, pages 129-142, especially on pages 130-132.

Preferred DPP-IV inhibitors are those described by Mona Patel and col. (Expert Opinion Investig Drugs. 2003 April; 12(4):623-33) on the paragraph 5, especially P32/98, K-364, FE-999011, BDPX, NVP-DDP-728 and others, which publication is hereby incorporated by reference especially the described DPP-IV inhibitors.

Another preferred DPP-IV inhibitor is the No. 815541 (T 6666) from Tanabe.

Preferred DPP-IV inhibitors are also described in the patent applications WO 02/083128, especially the compounds described in the examples 1 to 13, U.S. Pat. No. 6,395,767 examples 1 to 109 and WO 03/033671 all the specifically described compounds e.g. compounds 1 to 393, compounds of pages 67-70.

FE-999011 is described in the patent application WO 95/15309 page 14, as compound No. 18.

Another preferred inhibitor is the compound BMS-477118 disclosed in WO 2001068603 or U.S. Pat. No. 6,395,767 (compound of example 60) also known as is (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) as depicted in Formula M of the patent application WO 2004/052850 on page 2, and the corresponding free base, (1S,3S,5S)-2-[(2S)-2-amino-2-(3-hydroxy-tricyclo[3.3.1.1$^{3,7}$]dec-1-yl)-1-oxoethyl]-2-azabicyclo-[3.1.0]hexane-3-carbonitrile (M') and its monohydrate (M") as depicted in Formula M of the patent application WO 2004/052850 on page 3. The compound BMS-477118 is also known as saxagliptin.

Another preferred inhibitor is the compound GSK23A disclosed in WO 03/002531 (example 9) also known as (2S,4S)-1-((2R)-2-Amino-3-[(4-methoxybenzyl)sulfonyl]-3-methylbutanoyl)-4-fluoropyrrolidine-2-carbonitrile hydrochloride.

P32/98 (CAS number: 251572-86-8) also known as 3-[(2S,3S)-2-amino-3-methyl-1-oxopentyl]thiazolidine can be used as 3-[(2S,3S)-2-amino-3-methyl-1-oxopentyl]thiazolidine and (2E)-2-butenedioate (2:1) mixture and is described in WO 99/61431 and the below formula,

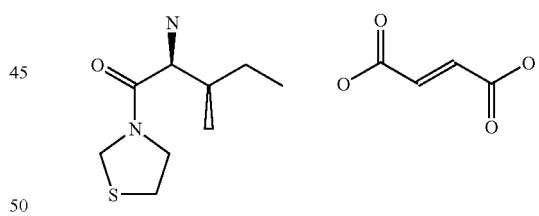

is described in WO 99/61431 and also in Diabetes 1998, 47, 1253-1258, in the name of Probiodrug, as well as the compound P93/01 described by the same company.

Other very preferred DPP-IV inhibitors are the compounds disclosed in the patent application WO 02/083128 such as in the claims 1 to 5. Most preferred DPP-IV inhibitors are the compounds specifically described by the examples 1 to 13 and the claims 6 to 10.

Other very preferred DPP-IV inhibitors are the compounds disclosed By Bristol-Myers Squibb such as Saxagliptin (BMS477118).

Other very preferred DPP-IV inhibitors of the invention are described in the International patent application WO 02/076450 (especially the examples 1 to 128) and by Wallace T. Ashton (Bioorganic & Medicinal Chemistry Letters 14 (2004) 859-863) especially the compound 1 and the compounds listed in the tables 1 and 2. The preferred compound is the compound 21e (table 1) of formula:

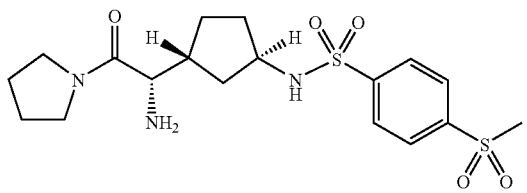

Other preferred DPP-IV inhibitors are described in the patent applications WO 2004/037169 especially those described in the examples 1 to 48 and WO 02/062764 especially the described examples 1 to 293, even preferred are the compounds 3-(aminomethyl)-2-isobuthyl-1-oxo-4-phenyl-1,2-dihydro-6-isoquinolinecarboxamide and 2-{[3-(aminomethyl)-2-isobuthyl-4-phenyl-1-oxo-1,2-dihydro-6-isoquinolyl]oxy}acetamide described on page 7 and also in the patent application WO2004/024184 especially in the reference examples 1 to 4.

Other preferred DPP-IV inhibitors are described in the patent application WO 03/004498 especially examples 1 to 33 and most preferably the compound of the formula

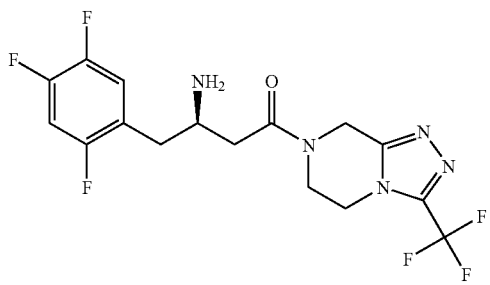

MK-0431 described by the example 7 and also known as MK-0431.

In each case in particular in the compound claims and the final products of the working examples, the subject matter of the final products, the pharmaceutical preparations and the claims are hereby incorporated into the present application by reference to these publications.

Preferred DPP-IV inhibitors are also described in the patent application WO 2004/037181 especially examples 1 to 33 and most preferably the compounds described in the claims 3 to 5.

Preferred DPP-IV inhibitors are N-substituted adamantyl-amino-acetyl-2-cyano pyrrolidines, N (substituted glycyl)-4-cyano pyrrolidines, N-(N'-substituted glycyl)-2-cyanopyrrolidines, N-aminoacyl thiazolidines, N-aminoacyl pyrrolidines, L-allo-isoleucyl thiazolidine, L-threo-isoleucyl pyrrolidine, and L-allo-isoleucyl pyrrolidine, 1-[2-[(5-cyanopyridin-2-yl)amino]ethylamino]acetyl-2-cyano-(S)-pyrrolidine, MK-431 and pharmaceutical salts thereof.

Most preferred DPP-IV inhibitors are selected from [S]-1-[2-(5-cyano-2-pyridinylamino)ethylamino]acetyl-2-pyrrolidine carbonitrile monohydrochloride, (S)-1-[(3-hydroxy-1-adamantyl)amino]acetyl-2-cyano-pyrrolidine and L-threo-isoleucyl thiazolidine (compound code according to Probiodrug: P32/98 as described above), MK-0431, 3-(aminomethyl)-2-isobuthyl-1-oxo-4-phenyl-1,2-dihydro-6-isoquinolinecarboxamide and 2-{[3-(aminomethyl)-2-isobuthyl-4-phenyl-1-oxo-1,2-dihydro-6-isoquinolyl]oxy}acetamide and optionally pharmaceutical salts thereof.

[S]-1-[2-(5-cyano-2-pyridinylamino)ethylamino]acetyl-2-pyrrolidine carbonitrile monohydrochloride and (S)-1-[(3-hydroxy-1-adamantyl)amino]acetyl-2-cyano-pyrrolidine are specifically disclosed in Example 3 of WO 98/19998 and Example 1 of WO 00/34241, respectively. The DPP-IV inhibitor P32/98 (see above) is specifically described in Diabetes 1998, 47, 1253-1258. [S]-1-[2-(5-cyano-2-pyridinylamino)ethylamino]acetyl-2-pyrrolidine carbonitrile monohydrochloride and (S)-1-[(3-hydroxy-1-adamantyl)amino]acetyl-2-cyano-pyrrolidine can be formulated as described on page 20 of WO 98/19998 or in WO 00/34241.

Especially preferred are 1-{2-[(5-cyanopyridin-2-yl)amino]ethylamino}acetyl-2-(S)-cyano-pyrrolidine (also named [S]-1-[2-(5-cyano-2-pyridinylamino)ethylamino]acetyl-2-pyrrolidine carbonitrile monohydrochloride), of formula:

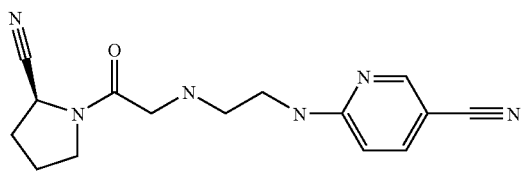

especially the dihydrochloride and monohydrochloride form thereof, pyrrolidine, 1-[(3-hydroxy-1-adamantyl)amino]acetyl-2-cyano-, (S) (also named (S)-1-[(3-hydroxy-1-adamantyl)amino]acetyl-2-cyano-pyrrolidine, LAF237 or vildagliptin) of formula

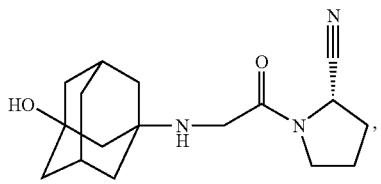

and L-threo-isoleucyl thiazolidine (compound code according to Probiodrug: P32/98 as described above), MK-0431, GSK23A, saxagliptin, 3-(aminomethyl)-2-isobuthyl-1-oxo-4-phenyl-1,2-dihydro-6-isoquinolinecarboxamide and 2-{[3-(aminomethyl)-2-isobuthyl-4-phenyl-1-oxo-1,2-dihydro-6-isoquinolyl]oxy}acetamide and optionally in any case pharmaceutical salts thereof.

DPP728 and LAF237 are specifically disclosed in Example 3 of WO 98/19998 and Example 1 of WO 00/34241, respectively. The DPP-IV inhibitor P32/98 (see above) is specifically described in Diabetes 1998, 47, 1253-1258. DPP728 and LAF237 can be formulated as described on page 20 of WO 98/19998 or in WO 00/34241, or in the International Patent Application No. EP2005/000400 (application number).

Any of the substances disclosed in the above mentioned patent documents or scientific publications, hereby included by reference, are considered potentially useful as DPP-IV inhibitors to be used in carrying out the present invention.

DPP-IV inhibitor to be used alone according to the present invention can be used in association with a carrier.

A carrier in the instant context is a tool (natural, synthetic, peptidic, non-peptidic) for example a protein which transports specific substances through the cell membrane in which it is embedded and into the cell. Different carriers (natural, synthetic, peptidic, non-peptidic) are required to transport different substances, as each one is designed to recognize only one substance, or group of similar substances.

Any means of detection known by the person skilled in the art can be used to detect the association of the DPP-IV with a carrier, for example, by labelling the carrier.

The DPP-IV inhibitor can be a peptidic or, preferably, non-peptidic one.

Most preferred are orally active DPP-IV inhibitors and pharmaceutical salts thereof.

The active ingredients (metformin or DPP-IV inhibitors) or pharmaceutically acceptable salts thereof according to the present invention may also be used in form of a solvate, such as a hydrate or including other solvents, used for crystallization.

It has now been surprisingly found that DPP-IV inhibitors especially LAF237 can be used in combination with Metformin to maintain lower blood glucose levels and/or lower glycosylated hemoglobin (HbA1c) level over an extended period of time.

Thus in a first embodiment, this invention provides a method for controlling glucose levels over an extended period of time comprising administering a therapeutically effective amount of metformin and a DPP-IV inhibitor to a patient in need thereof.

This invention further provides a method for controlling glycosylated hemoglobin (HbA1c) levels over an extended period of time comprising administering a therapeutically effective amount of metformin and a DPP-IV inhibitor to a patient in need thereof.

Or the use of metformin in combination with a DPP-IV inhibitor for the manufacture of a medicament for controlling the blood HbA1c or glucose level over an extended period of time in a patient in need thereof.

The invention also relates to a method for maintaining glucose or glycosylated hemoglobin (HbA1c) levels over an extended period of time comprising administering a therapeutically effective amount of metformin and a DPP-IV inhibitor to a patient in need thereof Preferably the DPP-IV inhibitor is (S)-1-[(3-hydroxy-1-adamantyl)amino]acetyl-2-cyano-pyrrolidine (LAF237 or vildagliptin) of formula (I)

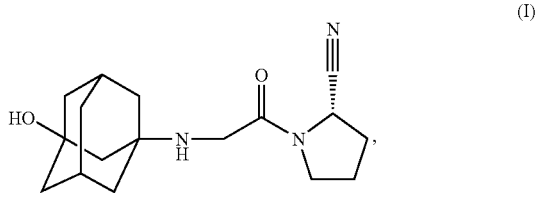

(I)

or pharmaceutically acceptable salt thereof.

In the present context the terms "(S)-1-[(3-hydroxy-1-adamantyl)amino]acetyl-2-cyano-pyrrolidine" or "LAF237" or "vildagliptin" is also intended to comprise any salt or crystal form thereof.

Preferably the treated patient is suffering from hyperglycemia. Most preferably the patient is suffering from a disease selected from diabetes mellitus, type I or insulin-dependent diabetes mellitus (IDDM), type II or non-insulin-dependent diabetes mellitus (NIDDM), type A insulin resistance, IGM, IFG or IGT. In a preferred embodiment the patient is suffering from type II diabetes or IGT.

In a most preferred embodiment the DPP-IV inhibitor is added to the standard diabetes treatment in patients whose disease was not adequately controlled by metformin alone.

The present methods or uses are particularly useful for the prevention or delay of progression of conditions associated with type II diabetes or IGT, particularly cardiovascular and microvascular conditions.

The invention furthermore relates to the use of metformin in combination with a DPP-IV inhibitor for the manufacture of a medicament to control the blood HbA1c or glucose level over an extended period of time in the treated patient, particularly in a patient (e.g. type II diabetic patient) not adequately controlled by metformin alone.

Preferably the invention relates to the use of metformin in combination with a DPP-IV inhibitor for the manufacture of a medicament to control the blood HbA1c or glucose level over an extended period of time in a patient (e.g. type II diabetic patient) not adequately controlled by metformin alone.

The term "control" means that the glucose level or the HbA1c level in the blood does not increase more than 8%, preferably less than 5%, more preferably less than 3%, even more preferably less than 2%, most preferably less than 1.5% or 1.2% from baseline lower glucose level or lower HbA1c level reached with the used combination therapy (see examples 1 or 2).

The term "over an extended period of time" means at least 10 months, preferably at least 12 months, or at least 18 months.

Furthermore as used herein, "a daily dose" means the dose given within a 24-hour period.

The term "prevention" means prophylactic administration of the combination to healthy patients to prevent the outbreak of the conditions mentioned herein. Moreover, the term "prevention" means prophylactic administration of such combination to patients being in a pre-stage of the conditions, to be treated.

The term "delay of progression" used herein means administration of the combination, such as a combined preparation or pharmaceutical composition, to patients being in a pre-stage of the condition to be treated in which patients a pre-form of the corresponding condition is diagnosed.

By the term "treatment" is understood the management and care of a patient for the purpose of combating the disease, condition, or disorder.

As used herein, the term "patient" refers to an animal who is suffering from hyperglycemia or diabetes or IGM. The preferred animal is a mammal, such as dogs, cats, horses, cows and humans. It is preferred that the patient is a human.

In this field the preferred patient population age is from 45 years onwards, most preferred from 60 years onwards.

The person skilled in the pertinent art is fully enabled to select a relevant test model and protocols to prove the beneficial effects of the invention.

Monitoring of glycemic status, as performed by patients and health care providers, is well known in the art such as reported in Diabetes Care "*Tests of Glycemia in Diabetes—American Diabetes Association*" 2003 26: S106-108 and described below. This publication is hereby incorporated by reference in their entirety.

The American Diabetes Association's technical review should be consulted for further information (e.g. Goldstein D E, Little R R, Lorenz R A, Malone J I, Nathan D, Peterson C M: Tests of glycemia in diabetes (Technical Review). *Diabetes Care* 18:896-909, 1995).

Within only a few years, self-monitoring of blood glucose (SMBG) by patients has revolutionized management of diabetes. Using SMBG, patients with diabetes can work to achieve and maintain specific glycemic goals.

The subject of SMBG has been addressed extensively by two American Diabetes Association Consensus Conferences, which provide a comprehensive review of the subject (American Diabetes Association: Self-monitoring of blood glucose (Consensus Statement). *Diabetes Care* 17:81-86, 1994— and—American Diabetes Association: Self-monitoring of blood glucose (Consensus Statement). *Diabetes Care* 10:93-99, 1987)

SMBG has supplanted urine glucose testing for most patients. Urine glucose testing by patients in the home setting consists of semiquantitative measurements based on single voidings or, less often, by more quantitative "blocks" collected over 4-24 h. The rationale is that urinary glucose values reflect mean blood glucose during the period of urine collection. Blood and urine glucose testing and urine ketone testing provide useful information for day-to-day management of diabetes.

However, these tests cannot provide the patient and health care team with a quantitative and reliable measure of glycemia over an extended period of time. Measurements of glycated proteins, primarily hemoglobin and serum proteins, have added a new dimension to assessment of glycemia. With a single measurement, each of these tests can quantify average glycemia over weeks and months, thereby complementing day-to-day testing.

Glycated Hemoglobin (GHb) Testing:

GHb, also referred to as glycohemoglobin, glycosylated hemoglobin, $HbA_{1c}$, or $HbA_1$, is a term used to describe a series of stable minor hemoglobin components formed slowly and nonenzymatically from hemoglobin and glucose. The rate of formation of GHb is directly proportional to the ambient-glucose concentration. Since erythrocytes are freely permeable to glucose, the level of GHb in a blood sample provides a glycemic history of the previous 120 days, the average erythrocyte life span. GHb most accurately reflects the previous 2-3 months of glycemic control.

Many different types of GHb assay methods are available to the routine clinical laboratory e.g. $HbA_{1c}$ can be measured by High Performance Liquid Chromatography (HPLC) using the ion-exchange method on a Bio-Rad Diamat analyzer. A back-up affinity method are used if hemoglobin variants or hemoglobin degradation peaks are observed.

Methods differ considerably with respect to the glycated components measured, interferences, and nondiabetic range. Glycated hemoglobin is often reported as hemoglobin $A_{1c}$-$HbA_{1c}$, has become the preferred standard for assessing glycemic control. In referring to this test, the term "A1C test" will be used.

A1C testing should be performed routinely in all patients with diabetes, first to document the degree of glycemic control at initial assessment, then as part of continuing care. Since the A1C test reflects a mean glycemia over the preceding 2-3 months, measurement approximately every 3 months is required to determine whether a patient's metabolic control has reached and been maintained within the target range.

The A1C test has been shown to predict the risk for the development of many of the chronic complications in diabetes, analogous to using cholesterol determinations to predict the risk for development of cardiovascular disease.

Glycated Serum Protein (GSP)

Because the turnover of human serum albumin is much shorter (half-life of 14-20 days) than that of hemoglobin (erythrocyte life span of 120 days), the degree of glycation of serum proteins (mostly albumin) provides an index of glycemia over a shorter period of time than does glycation of hemoglobin. Measurements of total GSP and glycated serum albumin (GSA) correlate well with one another and with measurements of glycated hemoglobin (A1C test). In situations where the A1C test cannot be measured or may not be useful (e.g., hemolytic anemias), the GSP assay may be of value in the assessment of the treatment regimen. Several methods have been described that quantify either total GSP or total GSA. One of the most widely used is called the fructosamine assay. Values for GSP vary with changes in the synthesis or clearance of serum proteins, that can occur with acute systemic illness or with liver disease. In addition, there is continuing debate as to Whether fructosamine assays should be corrected for serum protein or serum albumin concentrations.

A single measurement of GSP provides an index of glycemic status over the preceding 1-2 weeks, while a single A1C test provides an index of glycemic status over a considerably longer period of time, 2-3 months.

Measurement of GSP, regardless of the specific assay method, should not be considered equivalent to the A1C test, since it only indicates glycemic control over a short period of time. Therefore, GSP assays would have to be performed on a monthly basis to gather the same information as measured by the A1C test three to four times a year. Unlike the A1C test, GSP has not yet been shown to be related to the risk of the development or progression of chronic complications of diabetes.

Thus regular review of the glucose level or glycated haemoglobin (HbA1c) level progression should be checked every 3-6 months, according to the current guidelines for treatment of diabetes especially type 2 diabetes mellitus.

The glucose level progression checks (e.g. GSP assay, A1C, insulin) are well known by the physicians and reported in the art e.g. by the American Diabetes Association.

The applicant has surprisingly discovered that regular review of the glucose level or glycated haemoglobin (HbA1c) level progression checks can be reduced from 2 to 3 times annually to only one check annually or one every 18 months. Thus the costs that diabetic patients bear are decreased.

Therefore in a further embodiment, the present invention relates to a method for monitoring the glucose level in an patient comprising treating the patient with a pharmaceutically effective amount of metformin or a pharmaceutically acceptable salt thereof in combination with a DPP-IV inhibitor or a pharmaceutically acceptable salt thereof and checking the patient's glucose level on an annual basis (i.e. once a year) or once every 18 months.

In a preferred aspect, the present invention relates to a method for monitoring the glycated haemoglobin level in an patient comprising treating the patient with a pharmaceutically effective amount of metformin or a pharmaceutically acceptable salt thereof in combination with a DPP-IV inhibitor or a pharmaceutically acceptable salt thereof and checking the patient's glycated haemoglobin level on an annual basis or once every 18 months.

Method of monitoring as described above, wherein the glucose progression checks, the glycated haemoglobin level checks or the A1C test have to be assessed by the physician only on an annual basis or once every 18 months.

The glucose progression checks can be performed e.g. by A1C tests, GSP assays, etc.

Method of Monitoring as described above, wherein the progression checks of patient's glucose level or glycated haemoglobin level e.g. the A1C test, have to be carried out only on an annual basis or once every 18 months.

Method of monitoring as described above, wherein the patient is reminded (e.g. via mail or e-mail) to perform a glucose progression check or a glycated haemoglobin level check e.g. the A1C test the A1C test only on an annual basis or once every 18 months.

In another embodiment, the present invention relates to a method for adjusting therapy in an patient comprising treating the patient with a pharmaceutically effective amount of metformin or a pharmaceutically acceptable salt thereof in combination with a DPP-IV inhibitor or a pharmaceutically acceptable salt thereof; and changing a treatment regimen in said patient, based on an annual progression check of patient's glucose level(s) or glycated haemoglobin level(s) e.g. annual A1C test.

In the present application, the treatment regimen or therapy is adjusted/changed only if necessary, based on the result of the annual (or every 18 months) progression checks.

The invention also relates to the use of metformin in combination with a DPP-IV inhibitor for the manufacture of a medicament for the treatment of hyperglycemia, preferably type 2 diabetes, wherein the treatment regimen in said patient is changed or adapted based, if necessary, on an annual progression check of patient's glucose level or glycated haemoglobin level e.g. annual A1C test.

In a third embodiment, the present invention relates to a method for adjusting therapy in an patient treated with metformin in combination with a DPP-IV inhibitor wherein the physician reevaluates and if necessary changes the treatment regimen in said treated patient, based on an annual progression check of patient's glucose level or annual A1C test, or once every 18 months. Or to the use of metformin in combination with a DPP-IV inhibitor for the manufacture of a medicament for the treatment of hyperglycemia, preferably type 2 diabetes, wherein the physician reevaluates and if necessary changes the treatment regimen in said treated patient, based on an annual progression check of patient's glucose level or or glycated haemoglobin level e.g. annual A1C test (or once every 18 months).

The invention in a further aspect relates to the use of a A1C test to monitor the glycated haemoglobin (HbA1c) level in a blood sample, wherein said blood sample is collected from a patient treated with metformin combination with a DPP-IV inhibitor, and wherein the A1C test is performed on an annual basis or once every 18 months.

The invention in a further aspect relates to a method for the treatment or prevention of type 2 diabetes, comprising administering daily, a therapeutically effective amount of metformin, preferably 1500 to 2000 mg of metformin or a pharmaceutically acceptable salt thereof and 50 mg of (S)-1-[(3-hydroxy-1-adamantyl)amino]acetyl-2-cyano-pyrrolidine or a pharmaceutically acceptable salt thereof to a patient in need thereof.

The invention also relates to a treatment regimen, for the treatment of type 2 diabetes wherein,
i) 50 mg of (S)-1-[(3-hydroxy-1-adamantyl)amino]acetyl-2-cyano-pyrrolidine is to be administered in combination to metformin, preferably 1500 to 2000 mg of metformin, daily, preferably for at least a period of 12 months to a patient in need thereof,
ii) the treatment regimen of metformin and (S)-1-[(3-hydroxy-1-adamantyl)amino]acetyl-2-cyano-pyrrolidine in said patient, being not modified before the end of a 12 month period.

In the above described treatment regimen, the term "daily", applies to metformin and (S)-1-[(3-hydroxy-1-adamantyl) amino]acetyl-2-cyano-pyrrolidine (vildagliptin).

The invention also relates to a treatment regimen, for the treatment of type 2 diabetes wherein, i) an effective amount of metformin, preferably 1500 to 2000 mg of metformin is to be administered daily, as the starting point of the treatment for a period of time,
ii) once administration of metformin does not stabilize the glucose level or glycated haemoglobin level anymore, 50 mg of (S)-1-[(3-hydroxy-1-adamantyl)amino]acetyl-2-cyano-pyrrolidine is to be administered (daily) in combination to metformin (daily) (preferably at an unchanged dosage, preferably 1500 to 2000 mg of metformin), daily, preferably for a period of at least 12 months,
iii) the treatment regimen of metformin and (S)-1-[(3-hydroxy-1-adamantyl)amino]acetyl-2-cyano-pyrrolidine in said patient, being not modified before the end of a 12 month period.

The invention also relates to the use of metformin in combination with (S)-1-[(3-hydroxy-1-adamantyl)amino]acetyl-2-cyano-pyrrolidine in the manufacture of a medicament for the treatment of type 2 diabetes wherein, 50 mg of (S)-1-[(3-hydroxy-1-adamantyl)amino]acetyl-2-cyano-pyrrolidine is to be administered in combination to metformin, preferably 1500 to 2000 mg of metformin, daily, to a patient in need thereof.

The invention also relates to the use of metformin in combination with (S)-1-[(3-hydroxy-1-adamantyl)amino]acetyl-2-cyano-pyrrolidine in the manufacture of a medicament for the treatment of type 2 diabetes wherein,
i) 50 mg of (S)-1-[(3-hydroxy-1-adamantyl)amino]acetyl-2-cyano-pyrrolidine is to be administered in combination to metformin, preferably 1500 to 2000 mg of metformin, daily, preferably for a period of at least 12 months to a patient in need thereof,
ii) the treatment regimen of metformin and (S)-1-[(3-hydroxy-1-adamantyl)amino]acetyl-2-cyano-pyrrolidine in said patient, being not modified before the end of a 12 month period.

The invention also relates to the use of metformin in combination with (S)-1-[(3-hydroxy-1-adamantyl)amino]acetyl-2-cyano-pyrrolidine in the manufacture of a medicament for the treatment of type 2 diabetes wherein,
i) an effective amount of metformin is to be administered as the starting point of the treatment for a period of time,
ii) once administration of metformin does not stabilize the glucose level or glycated haemoglobin level anymore, 50 mg of (S)-1-[(3-hydroxy-1-adamantyl)amino]acetyl-2-cyano-pyrrolidine is to be administered in combination to metformin, preferably 1500 to 2000 mg of metformin, daily, preferably for a period of at least 12 months,
iii) the treatment regimen of metformin and (S)-1-[(3-hydroxy-1-adamantyl)amino]acetyl-2-cyano-pyrrolidine in said patient, being not modified before the end of a 12 month period.

Preferably the treated patient in the above described methods or uses, is suffering from hyperglycemia, Most preferably the patient suffering from hyperglycemia, suffering from a disease selected from diabetes mellitus, type I or insulin-dependent diabetes mellitus (IDDM), type II or non-insulin-dependent diabetes mellitus (NIDDM), type A insulin resistance, IGM, IFG or IGT. In a preferred embodiment the patient is suffering from type II diabetes or IGT. In another preferred embodiment the treated patient is a patient whose disease was not adequately controlled by metformin alone.

Use, method or treatment regimen according to the present invention, wherein a progression check of patient's glucose level or glycated haemoglobin level e.g. the A1C test, is carried out on an annual basis or once every 18 months.

Use, method or treatment regimen according to the present invention, wherein 1500 to 2000 mg of metformin or a pharmaceutically acceptable salt thereof in combination with 50 mg of (S)-1-[(3-hydroxy-1-adamantyl)amino]acetyl-2-cyano-pyrrolidine or a pharmaceutically acceptable salt thereof, are administered daily to a patient in need thereof.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The herein described pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 90%, preferably of from about 1% to about 80%, of the active compound.

Pharmaceutical preparations for enteral or parenteral, and also for ocular, administration are, for example, in unit dose forms, such as coated tablets, tablets, capsules or suppositories and also ampoules. These are prepared in a manner that is known per se, for example using conventional mixing, granulation, coating, solubulizing or lyophilising processes. Thus, pharmaceutical preparations for oral use can be obtained by combining the active compound with solid excipients, if desired granulating a mixture which has been obtained, and, if required, or necessary, processing the mixture or granulate into tablets or coated tablets cores after having added suitable auxiliary substances.

The dosage of the active compound can depend on a variety of factors, such as mode of administration, homeothermic species, age and individual condition.

Preferred dosages, for those active ingredients of the pharmaceutical combination according to the present invention that are commercially available, are especially therapeutically effective commercially available dosages.

The dosage of the active compound can depend on a variety of factors, such as mode of administration, homeothermic species, age and/or individual condition.

By the terms "treatment regimen is changed or adapted" or "adjusting therapy" the person skilled of the art would understand e.g. modification of the dosage of the active ingredients, addition of a third active ingredient especially a hypoglycemic agent such as a glitazone (pioglitazone or rosiglitazone) or insulin, or modification of the treatment schedule e.g. by reducing or increasing the administration of one active ingredient e.g. metformin once every two days.

The corresponding active ingredient or a pharmaceutically acceptable salt thereof may also be used in form of a hydrate or include other solvents used for crystallization.

The exact dosage will of course vary depending upon the compound employed, mode of administration and treatment desired. The compound may be administered by any conventional route, non-oral or preferably orally.

In general, satisfactory results are obtained when DPP-IV inhibitor especially LAF237 is administered at a daily dosage of from about 0.01 to 50 mg/kg, more preferred doses ranged from 0.1 to 50 mg/kg.

For the larger mammals, an indicated total daily dosage is in the range from about 0.01 to 100 mg/kg of the compound, conveniently administered in divided doses 2 to 4 times a day in unit dosage form containing for example from about 0.1 to about 50 mg of the compound in sustained release form.

Preferably for the DPP-IV inhibitor especially LAF237 an indicated total daily dosage is in the range from between 1 and 500 mg, preferably between 10 and 200 mg of active ingredient.

Another preferred DPP-IV inhibitor especially LAF237 daily oral dosage is between 1 and 100 mg preferably between 10 and 100 mg e.g. 10 mg, most preferably between 25 and 100 mg e.g. 25 mg or 30 or 40 or 50, 61, 70, 90,100 mg. The very preferred daily oral dosage of LAF237 is between 50 and 100 mg.

Appropriate unit doses for oral administration contain for example about 25 to about 100 mg of DPP-IV inhibitor especially LAF237, such as preferably 25, 50 or 100 mg. Appropriate doses for parenteral administration contain for example about 1 to about 100 mg of the compound, e.g. from 10 to 50 mg.

The DPP-IV inhibitor can also be administered every day or only every two days, or twice a week.

The preparation of metformin (dimethyldiguanide) and its hydrochloride salt is state of the art and was disclosed first by Emil A. Werner and James Bell, J. Chem. Soc. 121, 1922, 1790-1794. In general, satisfactory results are obtained when Metformin is administered at a daily dosage of from about 50 mg to about 3000 mg, preferably from about 500 mg to about 2000 mg. Metformin can be administered e.g. in the form as marketed e.g. as 500 mg tablets. If the drug metformin shall be administered in a separate pharmaceutical composition, it can be administered in the form as it is launched e.g. under the trademark DIABETOSAN™ or GLUCOPHAGE™. If the drug metformin shall be administered in a separate pharmaceutical composition in the form of its hydrochloride salt, the metformin hydrochloride salt can be administered in the form as it is launched e.g. under the trademarks DIABETASE 500™, DIABETASE™ 850™ or GLUCOPHAGE S™. Metformin can also be administered only every two days, or twice a week.

The compounds may be administered in similar manner to known standards for uses in these utilities. The suitable daily dosage for a particular compound will depend on a number of factors such as its relative potency of activity. A person skilled in the pertinent art is fully enabled to determine the therapeutically effective dosage.

The compound of the invention may be administered in free base for or as a pharmaceutically acceptable acid addition or quaternary ammonium salt. Such salts may be prepared in conventional manner and exhibit the same order of activity as the free forms. If these compounds have, for example, at least one basic center, they can form acid addition salts. Corresponding acid addition salts can also be formed having, if desired, an additionally present basic center. The compounds having an acid group (for example COOH) can also form salts with bases. For example, the compounds to be combined can be present as a sodium sale, as a maleate or as a dihydrochloride. The active ingredient or a pharmaceutically acceptable salt thereof may also be used in form of a hydrate or include other solvents used for crystallization.

The present invention refers to a combination which comprises a DPP-IV inhibitor in free or pharmaceutically acceptable salt form, and metformin or the pharmaceutically acceptable salt thereof and optionally at least one pharmaceutically acceptable carrier; wherein the active ingredients can be administered simultaneously or sequentially in any order, separately or in a fixed combination (same galenic formulation).

A combined preparation which comprises a DPP-IV inhibitor in free or pharmaceutically acceptable salt form and metformin and optionally at least one, i.e., one or more, e.g. two, pharmaceutically acceptable carrier for simultaneous, separate or sequential use is especially a "kit of parts" in the sense that the components, a DPP-IV inhibitor in free or pharmaceutically acceptable salt form and metformin, can be dosed independently or by use of different fixed combinations with distinguished amounts of the components, i.e. at different time points or simultaneously. The parts of the kit of parts can then, e.g., be administered simultaneously or chronologically staggered, that is at different time points and with equal or different time intervals for any part of the kit of parts. Preferably, the time intervals are chosen such that the effect on the treated disease or condition in the combined use of the parts is larger than the effect which would be obtained by use of only any one of the components.

A therapeutically effective amount of each of the components of the combination of the present invention may be administered simultaneously or sequentially and in any order, and the components may be administered separately or as a fixed combination. For example, the method of treatment of the invention may comprise (i) administration of a DPP-IV inhibitor in free or pharmaceutically acceptable salt form and (ii) administration of metformin simultaneously or sequentially in any order, in jointly therapeutically effective amounts, preferably in synergistically effective amounts, e.g. in daily dosages corresponding to the ratios described herein.

The pharmaceutical compositions according to the invention can be prepared in a manner known per se and are those suitable for enteral, such as oral or rectal, and parenteral administration to mammals (warm-blooded animals), including man, comprising a therapeutically effective amount of the pharmacologically active compound, alone or in combination with one or more pharmaceutically acceptable carries, especially suitable for enteral or parenteral application.

To further illustrate the invention, but not by way of limitation, the following clinical study is provided. Further experimental protocols are described in the patent application WO 01/52825 describing combinations comprising a DPP-IV inhibitor and an antidiabetic compound e.g. metformin.

The invention has been described above by reference to preferred embodiments but, as those skilled in the art will appreciate, many additions, omissions and modifications are possible all within the scope of the claims below.

All patents and literature references cited in this specification are hereby incorporated by reference in their entirety. In case of inconsistencies, the present description, including the definitions and interpretations, will prevail.

EXAMPLE 1

Clinical Study

This is a 40-week extension to core study, a 12-week randomized, parallel group, multi-center, placebo-controlled trial in patients with Type 2 diabetes who are already receiving metformin at a stable dosage of 1500-3000 mg daily. Patients treated with placebo, LAF237 50 mg OD (omnia die/once a day) in addition to metformin during the core study and maintained their treatment regimen in the extension. The main objective of the 40-week extension study is to assess the safety, tolerability and efficacy of long-term administration of LAF237 administered in combination with metformin.

1. Study Objectives:

Primary i) To evaluate the effect on $HbA_{1c}$ of additional therapy with LAF237 in patients with Type 2 diabetes mellitus already receiving metformin at a dosage of 1500-2000 mg daily.

ii) To evaluate the safety and tolerability of additional therapy with LAF237 in patients with Type 2 diabetes mellitus already receiving metformin at a dosage of 1500-2000 mg daily.

2. Overall Study Design

This randomized, parallel group placebo-controlled trial evaluates the efficacy, safety and tolerability of 52 weeks treatment with LAF237 in patients with Type 2 diabetes who are already receiving metformin at a stable dosage of 1500-2000 mg daily. All patients are randomized to receive either placebo or LAF237 (50 mg) once dally for 52 weeks in addition to metformin at an unchanged dosage.

During the 4-week run-in period, all patients receive LAF237 placebo tablets and are assessed for inclusion in the study. Patients meeting the inclusion criteria at the Baseline visit receives randomized treatment once daily for 52 weeks. The total study duration for each patient is 56 weeks. Throughout the study, patients are required to maintain their prior diet and exercise habits and to continue to take metformin at an unchanged dosage.

$HbA_{1c}$ and fasting plasma glucose, insulin, pro-insulin, C-peptide and lipids are measured at various times during the study. Hypoglycemia and other adverse events are be documented, as are laboratory evaluations (including amylase and lipase) and vital signs. In addition, a standard meal test are carried out at baseline (Visit 3) and again at the end of the study.

(i) Study Design

| | | Core Phase | | Extension Phase | |
|---|---|---|---|---|---|
| metformin | placebo OD | placebo OD | +metformin | placebo OD | +metformin |
| | +metformin | LAF 50 mg OD | +metformin | LAF 50 mg OD | +metformin |

| Visit | 1 | 2 | 3 | 4 | 5 | 6 | 7 | 8 | 9 | 10 | 11 | 12 |
|---|---|---|---|---|---|---|---|---|---|---|---|---|
| Weeks | -4 | -2 | B | 1 | 2 | 4 | 8 | 12 | 16 | 24 | 36 | 52 |

B = Baseline

3. Baseline Characteristics of Extension Patient Population

|  | metformin + LAF237 50 mg N = 42 | metformin + placebo N = 29 |
| --- | --- | --- |
| Gender (M/F %) | 62/38 | 76/24 |
| Mean age (years) (SD) | 58.4 (9.2) | 54.3 (12.2) |
| Mean BMI (kg/m$^2$) (SD) | 29.6 (3.7) | 29.9 (3.6) |
| Mean duration of Type 2 diabetes (years) (SD) | 5.8 (4.2) | 4.6 (3.6) |
| Mean HbA1c (%) (SD) | 7.6 (0.6) | 7.8 (0.6) |
| Mean FPG (mmol/L) (SD) | 9.6 (1.6) | 10.1 (1.8) |
| Mean metformin dose (mg) (SD) | 1794 (270) | 1785 (280) |
| Mean duration of metformin use (months) (SD) | 28.7 (24.0) | 23.7 (25.1) |

4. Treatments

Investigational Therapy and Reference Therapy

For the 4-week run-in period, LAF237 placebo tablets is provided. During the 52 week randomized treatment period, LAF237 and matching placebo tablets are dispensed in bottles. Each bottle contains sufficient medication to provide for treatment according to the study protocol and additional medication to allow for delayed visits.

Treatment is assigned via a randomization number. At Visit 3 (Baseline) the randomization number is assigned only after completion of the baseline standard meal test.

Treatment Assignment

After satisfying the Week-4 (Visit 1) inclusion/exclusion criteria, each patient receives a unique subject identification number. After meeting the Baseline (Visit 3) eligibility criteria, each patient is randomized to one of the treatment groups.

Blinding

LAF237 active medication and placebo are blinded by the use of tablets with identical taste, smell, and appearance.

5. Visit Schedule

Visits are scheduled at Weeks-4, -2, 0 (=Baseline), 1, 2, 4, 8, 12, 14, 24, 36 and 52. Deviations of ±3 days are allowed for Visits 1 to 5 and ±7 days for Visits 6 to 52. Within each period the original schedule (based on Visit 1 (Week-4) for the run-in period and on Visit 3 (Baseline) for the double-blind period) must be restored in case of deviation.

All blood samples for laboratory evaluations are drawn between 07.00 h and 10.00 h. Patients are instructed not to eat or drink anything (except water) for approximately 7 hours prior to each scheduled laboratory evaluation. Study medication should not be taken prior to study visits.

Efficacy Assessments

Change in $HbA_{1c}$ from Baseline to week 12 or 52 compared to placebo (i.e. metformin alone). This is measured by using Tosoh ion exchange High Performance Liquid Chromotography (HPLC). Primus Affinity HPLC is used as a back-up method if hemoglobin variants or hemoglobin degradation peaks are observed.

Safety Assessments

Safety assessments consist of monitoring and recording all non-serious and serious adverse events (SAE), the regular monitoring of hematology, blood chemistry and urinalysis values, regular measurement of vital signs, the performance of physical examinations and body weight measurements.

Laboratory Evaluations

All laboratory samples are sent to a central laboratory for analysis.

Blood chemistry: Includes albumin, amylase (see note), alkaline phosphatase, bicarbonate, total bilirubin, BUN, C-reactive protein, calcium, chloride, LDL, HDL, total cholesterol, creatinine, CPK (see note), γ-GT, glucose, LDH, inorganic phosphorus, lipase, potassium, total protein, AST, ALT, sodium, triglycerides, uric acid and VLDL.

6. Statistical Methods

Statistical Methods:

The primary aim of the study is to evaluate the effect on HbA1c of additional therapy with LAF237 after 52 weeks of double blind treatment in patients with Type 2 diabetes mellitus already receiving metformin at a dosage of 1500-2000 mg daily. Patients will be randomized to placebo or LAF237 (50 mg) once daily for 52 weeks in addition to metformin at an unchanged dosage.

Populations:

Randomized: all patients who received a randomization number.

Intention to treat (ITT): all randomized patients who received trial medication and had at least one post-baseline efficacy measurement.

Safety: all randomized patients who received trial medication and had at least one post-baseline safety measurement.

Completer Population: all ITT patients who complete the study and have a valid $HbA_{1c}$ measurement at Week 52.

Background and demographic characteristics: All demographic and background data are summarized by treatment group using contingency tables for the qualitative variables. Mean, standard deviation, median, minimum and maximum will be used for quantitative variables.

Baseline comparability among the treatment groups for demographic variables (as described above) and baseline efficacy variables ($HbA_{1c}$, fasting plasma glucose (FPG), insulin, pro-insulin, C-peptide, lipids, weight and daily dose of metformin) are examined using the Cochran-Mantel-Haenszel test for qualitative variables and an F-test for quantitative variables. (These p-values are provided for descriptive purposes, and are not to be considered to define any formal basis for determining factors which should be included in statistical analysis models.)

Study medication: Duration on double-blind treatment are summarized by treatment group for the randomized population. A summary table shows, by treatment group, what doses of metformin patients were taking when they entered the study.

Concomitant therapy: Prior and concomitant medications and significant non-drug therapies (as coded using the WHO dictionary) are summarized by treatment group.

Efficacy Evaluation

Efficacy Analysis

The primary efficacy variable is change from baseline in $HbA_{1c}$ at the end of the study. (This uses the last observation carried forward (LOCF) algorithm for subjects who did not have a Week 12 or 52 $HbA_{1c}$ measurement.)

The null hypotheses to be tested are:

$$H_{01}: \delta_{LAF50} = \delta_{Placebo} \text{ and } H_{02}: \delta_{LAF100} = \delta_{Placebo}$$

where δ is the change from baseline in the treatment group indicated by the subscript. An ANCOVA model is fitted including terms for treatment, baseline $HbA_{1c}$, centre and treatment by baseline interaction. The possibility of a treatment by centre interaction will be investigated, although the interaction term is not be included in the primary analysis model. Appropriate linear contrasts are used to test the two null hypotheses at the 2 sided 0.025 level. Mean change from baseline and difference between the two groups will be summarized showing p-values and confidence intervals.

The primary analysis uses the ITT population and is repeated in the completer population.

Figures are produced to show the mean $HbA_{1c}$ against time for each treatment group, and the change from baseline in $HbA_{1c}$ at each timepoint.

Subgroup Analysis

Summaries of absolute values and changes from baseline in $HbA_{1c}$ are also presented for the following sub-groups in the ITT (Intent to treat) population:

1) Baseline $HbA_{1c}$ (7.0-8.0%, >8.0-9.5%), 2) BMI (Body mass index) (<30 kg/m$^2$, ≧30 kg/m$^2$; evaluated using the Week-4 measurement), 3) Age (<65 years, ≧65 years; evaluated using the Week-4 measurement), 4) Sex, 5) Center Safety Evaluation The assessment of safety is based mainly on the frequency of adverse events and on the number of laboratory values that fall outside of pre-determined ranges. Other safety data (e.g. vital signs) will be considered as appropriate.

Laboratory data are summarized by presenting summary statistics of raw data and change from baseline values (means, medians, standard deviations, minimum, maximum) and by the flagging of notable values in data listings.

Records of hypoglycemic events are summarized by treatment group, event type and plasma glucose equivalent during the randomized treatment period.

Sample Size and Power Considerations

The primary analysis variable is change from baseline in $HbA_{1c}$. Assuming a power of 80%, an overall significance level of 5%, a clinically relevant difference of 0.6% in $HbA_{1c}$, a standard deviation of 0.9% (estimate taken from previous studies) and adjusting for multiple comparisons then 45 completed patients are required per treatment group. Assuming 10-15% of patients drop out, this implies 52 patients should be randomized per group.

Results:

| Efficacy result - $HbA_{1c}$ (%) change from baseline at endpoint for Extension ITT population | | | | |
|---|---|---|---|---|
| Treatment | N | LS mean (SE) | 95% CI | p-value |
| A: metformin + LAF237 50 mg | 42 | −0.50 (0.14) | | |
| B: metformin + placebo | 29 | 0.60 (0.17) | | |
| Difference in mean change (A − B) | | −1.10 (0.22) | (−1.53, −0.67) | <0.0001 |

LS = least squares,
SE = standard error,
CI = confidence interval

At study endpoint, the adjusted mean reduction from baseline for $HbA_{1c}$ in the metformin+LAF237 50 mg group was 0.5% (p=0.007), and the difference in adjusted mean changes between this and the Metformin+placebo group was 1.10% (p<0.0001).

The number (%) of responders, defined as the endpoint $HbA_{1c}$<7%, was 41.7% in the metformin+LAF237 50 mg group compared with 10.7% in the metformin+placebo group.

| HbA1c (%) change from baseline at endpoint - by baseline HbA1c category for Extension ITT population (below table) | | | | | | |
|---|---|---|---|---|---|---|
| | | metformin + LAF237 50 mg N = 42 | | | metformin + placebo N = 29 | |
| Sub-group | Category | n | BL mean | change (SD) | n | BL mean | change (SD) |
| HbA1c at baseline | <7.0% | 6 | 6.92 | −0.18 (0.34) | 1 | 6.95 | 0.95 (—) |
| | ≧7% and ≦8% | 25 | 7.42 | −0.41 (0.56) | 17 | 7.43 | 0.77 (0.70) |
| | >8% and ≦9% | 10 | 8.40 | −0.62 (1.08) | 11 | 8.39 | 0.29 (1.43) |

BL = baseline

| Raw Mean (±SE) HbA1c (%) over time (Extension ITT population - below table) | | | | | |
|---|---|---|---|---|---|
| WEEK | Number of patients | Mean HbA1c (%) | Variation | Standard error | Treatment |
| −4 | 41 | 7.724390244 | 0.41339024 | 0.10041259 | Metformin (Met) + LAF237 50 mg |
| −2 | 42 | 7.657142857 | 0.39909408 | 0.09747943 | MET + LAF 50 mg |
| 0 | 42 | 7.583333333 | 0.32239837 | 0.08761365 | MET + LAF 50 mg |
| 4 | 42 | 7254761905 | 030985482 | 0.08589235 | MET + LAF 50 mg |
| 8 | 42 | 7.10952381 | 0.37844367 | 0.09492399 | MET + LAF 50 mg |
| 12 | 42 | 7.05 | 0.35329268 | 0.09171549 | MET + LAF 50 mg |
| 16 | 42 | 7.069047619 | 0.39828688 | 0.0973808 | MET + LAF 50 mg |
| 24 | 40 | 7.055 | 0.43279487 | 0.10401861 | MET + LAF 50 mg |
| 36 | 36 | 7.083333333 | 0.51057143 | 0.11909047 | MET + LAF 50 mg |
| 52 | 33 | 7.13030303 | 0.58280303 | 0.13289356 | MET + LAF 50 mg |
| −4 | 29 | 7.937931034 | 0.41172414 | 0.11915278 | Met + Placebo |
| −2 | 29 | 7.820689655 | 0.34312808 | 0.10877501 | Met + Placebo |
| 0 | 29 | 7.734482759 | 0.34019704 | 0.10830943 | Met + Placebo |
| 4 | 29 | 7.589655172 | 0.27024631 | 0.09653413 | Met + Placebo |
| 8 | 29 | 7.606896552 | 0.31995074 | 0.10503706 | Met + Placebo |
| 12 | 29 | 7.765517241 | 0.40591133 | 0.11830867 | Met + Placebo |
| 16 | 28 | 7.832142857 | 0.53041005 | 0.13763436 | Met + Placebo |
| 24 | 29 | 7.896551724 | 0.71605911 | 0.15713591 | Met + Placebo |

-continued

Raw Mean (±SE) HbA1c (%) over time (Extension ITT population - below table)

| WEEK | Number of patients | Mean HbA1c (%) | Variation | Standard error | Treatment |
|---|---|---|---|---|---|
| 36 | 28 | 7.946428571 | 0.66406085 | 0.15400149 | Met + Placebo |
| 52 | 26 | 8.330769231 | 1.23661538 | 0.21808744 | Met + Placebo |

In this study, HbA1c levels, the primary long-term measure of glycemic control, decreased significantly when LAF237 was added to a patient's course of therapy, and this benefit was maintained for one year. Bringing patients to an ideal HbA1c level early in the disease process, and maintaining those levels for as long as possible, is critical in type 2 diabetes, making these finding, very unexpected and encouraging.

Patients who were part of the metformin plus LAF237 treatment arm sustained an HbA1c level that was an average of 1.1 percent lower than the group on metformin plus placebo. Glucose levels measured after 8-12 hours of fasting and 1-2 hours after eating a meal were also reduced in patients taking metformin plus LAF237 versus continued therapy with metformin alone. The metformin plus LAF237 group maintained lower HbA1c levels for one year. In contrast, researcher saw an increase in HbA1c in the metformin only group during the same period. LAF was found to be well tolerated with 76.2 and 89.7 percent of patients completing the 52 week investigation in the LAF237 plus metformin arm and metformin plus placebo arms respectively.

EXAMPLE 2

If the lower HbA1c level obtained in a patient treated with one of the herein described combination is 7.04%, and the HbA1c level after 52 weeks of treatment with said combination is 7.12%, the HbA1c level increased only by 1.13%, which is in line with our very preferred embodiments.

What is claimed is:

1. A treatment regimen, for the treatment of type 2 diabetes over an extended period of time of at least 12 months wherein,
   i) 50 mg of (S)-1-[(3-hydroxy-1-adamantyl)amino]acetyl-2-cyano-pyrrolidine or a pharmaceutically acceptable salt thereof is to be administered in combination with 1500 to 2000 mg of metformin or a pharmaceutically acceptable salt thereof, daily, for at least a period of 12 months to a patient in need thereof,
   ii) the treatment regimen of metformin and (S)-1-[(3-hydroxy-1-adamantyl)amino]acetyl-2-cyano-pyrrolidine in said patient, being not modified before the end of a 12 month period.

2. A treatment regimen, for the treatment of type 2 diabetes over an extended period of time of at least 12 months wherein,
   i) an effective amount of metformin, or a pharmaceutically acceptable salt thereof is to be administered daily, to a patient in need thereof, as the starting point of the treatment for a period of time,
   ii) once administration of metformin does not stabilize the glucose level or glycated haemoglobin level anymore, 50 mg of (S)-1-[(3-hydroxy-1-adamantyl)amino]acetyl-2-cyano-pyrrolidine or a pharmaceutically acceptable salt thereof is to be administered in combination with metformin, or a pharmaceutically acceptable salt thereof, for at least a period of 12 months,
   ii) the treatment regimen of metformin and (S)-1-[(3-hydroxy-1-adamantyl)amino]acetyl-2-cyano-pyrrolidine in said patient, being not modified before the end of a 12 month period.

3. A method for the treatment of type 2 diabetes over an extended period of time of at least ten months, said method comprising administering daily to a patient in need thereof, a therapeutically effective amount of metformin or a pharmaceutically acceptable salt thereof in combination with 50 mg of (S)-1-[(3-hydroxy-1-adamantyl)amino]acetyl-2-cyano-pyrrolidine or a pharmaceutically acceptable salt thereof.

* * * * *